United States Patent
Goudot et al.

(10) Patent No.: US 11,633,199 B2
(45) Date of Patent: Apr. 25, 2023

(54) APPARATUS FOR TREATING VASCULAR THROMBOSIS BY ULTRASOUNDS

(71) Applicant: CARDIAWAVE, Paris (FR)

(72) Inventors: Guillaume Goudot, Paris (FR); Mathieu Pernot, Paris (FR); Mickael Tanter, Bagneux (FR); Michael Vion, La Chaussee Saint Victor (FR)

(73) Assignee: CARDIAWAVE, Paris (FR)

(*) Notice: Subject to any disclaimer, the term of this patent is extended or adjusted under 35 U.S.C. 154(b) by 148 days.

(21) Appl. No.: 16/755,591

(22) PCT Filed: Oct. 18, 2018

(86) PCT No.: PCT/EP2018/078510
§ 371 (c)(1),
(2) Date: Apr. 12, 2020

(87) PCT Pub. No.: WO2019/081329
PCT Pub. Date: May 2, 2019

(65) Prior Publication Data
US 2021/0196295 A1     Jul. 1, 2021

(30) Foreign Application Priority Data
Oct. 23, 2017 (FR) ...................... 1759995

(51) Int. Cl.
*A61B 17/22* (2006.01)
*A61B 8/08* (2006.01)
(Continued)

(52) U.S. Cl.
CPC ........ *A61B 17/22012* (2013.01); *A61B 8/085* (2013.01); *A61B 8/4461* (2013.01);
(Continued)

(58) Field of Classification Search
CPC . A61B 17/22012; A61B 8/085; A61B 8/4461; A61B 8/488; A61B 8/54;
(Continued)

(56) References Cited

U.S. PATENT DOCUMENTS 4,986,275 A    1/1991  Ishida et al.
5,165,412 A *  11/1992 Okazaki ............. A61B 17/2258
                                                     600/439
(Continued)

FOREIGN PATENT DOCUMENTS

| CN | 104013444 A | 9/2014 |
| EP | 0 614 651 A1 | 9/1994 |
| WO | 2009/094554 A1 | 7/2009 |

OTHER PUBLICATIONS

Zhang et al., "Histotripsy thrombolysis on retracted clots", Ultrasound in Med. & Biol., vol. 42, Issue 8, pp. 1-16, Aug. 2016.
(Continued)

*Primary Examiner* — Hien N Nguyen
(74) *Attorney, Agent, or Firm* — BakerHostetler

(57) ABSTRACT

An apparatus for treating vascular thrombosis with ultrasound, includes a therapeutic ultrasonic transducer, suitable for generating focused ultrasonic waves that propagate along an emission axis; an imaging ultrasonic transducer associated with the therapeutic transducer; a means for moving the focal spot of the therapeutic ultrasonic transducer along the emission axis with respect to the imaging transducer; a motorized mechanical system for translating the transducers along at least a first axis parallel to the emission axis and a second axis perpendicular to the first; and an electronic control system for driving the motorized mechanical system and the means for moving the focal spot of the therapeutic transducer.

15 Claims, 1 Drawing Sheet

(51) Int. Cl.
*A61B 8/00* (2006.01)
*A61N 7/00* (2006.01)
*A61B 90/00* (2016.01)

(52) U.S. Cl.
CPC ............. *A61B 8/488* (2013.01); *A61B 8/54* (2013.01); *A61N 7/00* (2013.01); *A61B 2090/064* (2016.02); *A61B 2503/40* (2013.01); *A61N 2007/0091* (2013.01)

(58) Field of Classification Search
CPC .......... A61B 2090/064; A61B 2503/40; A61B 17/22004; A61B 2017/22001; A61B 2018/0041; A61B 2090/065; A61N 7/00; A61N 2007/0091; A61N 2007/0052; A61N 2007/0095; A61N 7/02
See application file for complete search history.

(56) References Cited

U.S. PATENT DOCUMENTS

| | | | |
|---|---|---|---|
| 5,520,188 A | 5/1996 | Hennige et al. | |
| 5,590,653 A * | 1/1997 | Aida | A61N 7/02 600/411 |
| 5,827,204 A | 10/1998 | Grandia et al. | |
| 8,137,274 B2 | 3/2012 | Weng et al. | |
| 8,277,398 B2 | 10/2012 | Weng et al. | |
| 2004/0138563 A1 | 7/2004 | Moehring et al. | |
| 2006/0004290 A1 | 1/2006 | Smith et al. | |
| 2007/0041961 A1* | 2/2007 | Hwang | A61K 38/363 424/94.64 |
| 2012/0022552 A1 | 1/2012 | Neff | |
| 2012/0029353 A1 | 2/2012 | Slayton et al. | |
| 2015/0374342 A1* | 12/2015 | Son | G01S 7/52049 600/439 |

OTHER PUBLICATIONS

Zhang et al. "Non-invasive thrombolysis using histotripsy in a porcine deep vein thrombosis model", Ultrasound in Med. & Biol., vol. 43, Issue 7, Jul. 2017.
Bader et al. "Efficacy of histotripsy combined with rt-PA in vitro", Phys. Med. Biol., vol. 61, Issue 14, Jul. 21, 2016.
English translation of Notification of First Office Action issued in Chinese Patent Application 2018800691059 dated Sep. 1, 2021.

* cited by examiner

APPARATUS FOR TREATING VASCULAR THROMBOSIS BY ULTRASOUNDS

CROSS-REFERENCE TO RELATED APPLICATIONS

This application is a National Stage of International patent application PCT/EP2018/078510, filed on Oct. 18, 2018, which claims priority to foreign French patent application No. FR 1759995, filed on Oct. 23, 2017, the disclosures of which are incorporated by reference in their entirety.

FIELD OF THE INVENTION

The invention relates to an apparatus for treating vascular thrombosis with ultrasound, and more particularly by histotripsy.

BACKGROUND

The occlusion of a vessel, vein or artery via an acute thrombosis process (formation of a clot, or thrombus) is a frequent and serious mechanism responsible for most of the causes of death in the world. In arteries, thrombosis is the origin of most strokes and myocardial infarctions. When it occurs in the venous network, thrombosis results in pain, edemas, and a risk of detachment of the clot, which could result in a pulmonary embolism. The persistence of the occlusion of the vein by a thrombus may, eventually, be responsible for a chronic venous insufficiency, which manifests itself via pain, edema and ulcers, which may be responsible for a substantial decrease in quality of life.

The principle of treatment of arterial or venous thrombosis is based on systemic anticoagulation, allowing extension of the thrombosis and embolic complications to be avoided. However, in the case of deep venous thrombosis, this treatment is ineffective against chronic venous insufficiency, because most often it does not allow the thrombosed vein to be recanalized. The use of a thrombolytic treatment may allow the occluded vein to be recanalized but systemic administration is dangerous because of the induction of hemorrhages. The use of this treatment is therefore not recommended in case of venous thrombosis without serious pulmonary embolism. The use of thrombolysis in situ, via local administration by catheter, allows systemic effects to be limited. These techniques are invasive and most often require a foreign device (most often a stent) to be implanted. Therefore, there is a risk locally (bleeding, infection) and a risk of occlusion further on because of the persistence of the endovascular devices. An alternative therapeutic approach consists in using ultrasonic waves, alone or in association with drugs. In particular, it is known to apply the technique known as histotripsy to break up clots so as to re-establish circulation through an obstructed blood vessel; "thrombotripsy" is then spoken of. Histotripsy consists in using intense and focused pulses of ultrasound to induce a localized cavitation that mechanically breaks up the targeted soft tissue.

Document U.S. Pat. No. 5,827,204 describes an ultrasound-based therapeutic apparatus that may especially be used for a thrombotripsy treatment. The apparatus comprises a therapeutic transducer associated with an imaging transducer, the two transducers being joined to an actuator allowing them to be moved in an axial direction.

International patent application WO 2009/094554 and the articles:

Xi Zhang et al. "Histotripsy thrombolysis on retracted clots", Ultrasound in Med. & Biol. Volume 42, Issue 8, August 2016, pages 1903-1918;

Xi Zhang et al. "Non-invasive thrombolysis using histotripsy in a porcine deep vein thrombosis model", Ultrasound in Med. & Biol. 43, Issue 7, July 2017; and disclose thrombotripsy techniques that have been validated by studies carried out in vitro and—in the 2017 article—in vivo on pigs.

In these cases the therapeutic ultrasound, at a frequency of 1 MHz, was applied by means of a multi-element "therapeutic" transducer of set focal length, at the center of which was arranged a transducer for imaging with ultrasound (echography). In the in vitro studies, both the transducers and the capillary tube modelling the vein to be treated were submerged in an acoustic coupling liquid. In the in vivo studies, the transducers were submerged in an acoustic coupling liquid confined by a bottomless bowl and a sheet made of plastic, which made contact with the skin of the animal. The imaging transducer allowed the vein awaiting treatment and the focal spot of the therapeutic transducer to be located, said spot being able to be seen because of the cloud of cavitation bubbles generated therein. Then the assembly consisting of the therapeutic transducer and the imaging transducer was moved mechanically until the focal spot coincided with the vein.

The article by K. B. Bader et al. "Efficacy of histotripsy combined with rt-PA in vitro", Phys. Med. Biol., 21 Jul. 2016 studies the optimal operating conditions for a method for treating venous thrombosis associating histotripsy and administration of thrombolytic drugs. Only in vitro studies using a multi-ring therapeutic transducer, an imaging transducer (dissociated from the preceding transducer) and a capillary tube modelling a vein, all of which were submerged in a coupling liquid, are presented.

Acoustic coupling via submergence of transducers in a liquid is impractical. Furthermore, the imaging sensor must necessarily be kept a distance from the skin of the patient, this degrading the quality of the acquired images. In addition, this distance does not remain constant—and the quality of the images is therefore variable. This decreases the precision, and therefore the effectiveness, of the treatment, and increases the risk of damaging the wall of the blood vessel subjected to the treatment with focused ultrasound.

SUMMARY OF THE INVENTION

The invention aims to overcome the aforementioned drawbacks of the prior art. More particularly it aims to provide an imaging-assisted thrombotripsy method that is simpler to implement, that allows a higher treatment precision to be achieved and that especially decreases the risk of damage to the wall of the blood vessel.

According to the invention, this aim is achieved by allowing, via mechanical and/or electronic means, the focal spot of the therapeutic ultrasonic transducer to be moved with respect to the imaging ultrasonic transducer along the emission axis. This allows the imaging transducer to be kept in contact with the surface of the human or animal body to be treated—or more generally at a substantially constant distance from the latter—during the scan of the region to be treated and, therefore, images of higher quality to be obtained. In turn, the higher quality of the images allows the wall of the blood vessel to be treated to be more precisely located, and therefore accidental damage thereof to be avoided.

According to one advantageous embodiment of the invention, this aim may also be achieved by virtue of the use of a therapeutic ultrasonic transducer operating at a frequency higher than or equal to 2 MHz, instead of a frequency of about 1 MHz as in the prior art. This allows a smaller and more stable focal spot to be obtained, allowing advantage to be fully taken of the better knowledge of the location of the wall of the blood vessel, in order to avoid damage thereto.

The subject of the invention is therefore an apparatus for treating vascular thrombosis with ultrasound, comprising:

a therapeutic ultrasonic transducer, suitable for generating focused ultrasonic waves that propagate along an emission axis;

an imaging ultrasonic transducer associated with the therapeutic ultrasonic transducer, suitable for acquiring two- or three-dimensional images of a region to be treated of a human or animal body, the region to be treated including a focal spot of the therapeutic ultrasonic transducer;

a means for moving the focal spot of the therapeutic ultrasonic transducer along the emission axis with respect to the imaging ultrasonic transducer;

a motorized mechanical system suitable for moving the therapeutic ultrasonic transducer and the imaging ultrasonic transducer translationally along at least a first axis of movement parallel to said emission axis, and translationally or rotationally along or about a second axis of movement not parallel to the first; and an electronic control system configured to:
  drive the motorized mechanical system so as to perform a scan of the region to be treated while keeping constant, with a predefined tolerance, a distance between the imaging ultrasonic transducer and a surface of the human or animal body; and
  drive the means for moving the focal spot of the therapeutic ultrasonic transducer so as to control the position of the focal spot along the emission axis during said scan.

According to particular embodiments of the invention:

The apparatus may also comprise a force sensor suitable for generating a signal indicative of a force exerted on the imaging ultrasonic transducer in a direction parallel to said emission axis, the electronic control system being configured to acquire this signal and to use it to drive the motorized mechanical system so as to keep said imaging ultrasonic transducer in contact with said surface of the human or animal body during the scan.

The electronic control system may also be configured to apply said imaging ultrasonic transducer against said surface of the human or animal body during the scan with a constant force.

The electronic control system may also be configured to analyze images acquired by the therapeutic ultrasonic transducer so as to detect the surface of said human or animal body in order to drive the motorized mechanical system during said scan.

The electronic control system may also be configured to drive the means for moving the focal spot of the therapeutic ultrasonic transducer in such a way that said focal spot follows a predefined path inside said human or animal body during the scan.

The electronic control system may also be configured to:
  a) drive the motorized mechanical system so as to perform a first scan of the region to be treated;
  b) during this first scan, acquire a plurality of images of said region while keeping the therapeutic ultrasonic transducer inactive;
  c) drive the motorized mechanical system so as to perform a second scan of the region to be treated;
  d) during this second scan, activate the therapeutic ultrasonic transducer and drive the means for moving its focal spot in such a way that said focal spot follows a predefined path inside said human body, which is identified from the images acquired during the first scan.

More particularly, the electronic control system may also be configured to:
  b1) analyze the images acquired during the first scan in order to identify a blood vessel in the region to be treated of said human or animal body; and
  b2) determine said predefined path inside said human body in such a way that it corresponds to said blood vessel.

Furthermore, the electronic control system may also be configured to drive the motorized mechanical system in such a way that, during the second scan, said blood vessel is located in a central portion of a field of view of the imaging ultrasonic transducer.

The electronic control system may also be configured to acquire a plurality of images of the region to be treated during the second scan and to use these images to drive the motorized mechanical system.

The therapeutic ultrasonic transducer may be a multi-element transducer and the means for moving its focal spot comprises an electronic beam former configured to drive the elements of said transducer with variable delays in order to emit the focused ultrasonic waves with an adjustable focal length. More particularly, it may be a concentric multi-ring transducer.

The means for moving the focal spot of the therapeutic ultrasonic transducer may comprise a mechanical system allowing a relative movement, along said emission axis, of the therapeutic ultrasonic transducer and of the imaging ultrasonic transducer.

The imaging ultrasonic transducer may extend beyond, in a direction parallel to said emission axis, the therapeutic ultrasonic transducer.

The imaging ultrasonic transducer may be arranged at the center of the therapeutic ultrasonic transducer.

The apparatus may also comprise an acoustic interface device suitable for coupling the focused ultrasonic waves generated by the therapeutic ultrasonic transducer to said surface of the human or animal body.

Said motorized mechanical system may have three degrees of freedom translationally and three degrees of freedom rotationally.

Said therapeutic ultrasonic transducer may be suitable for generating focused ultrasonic waves at a frequency higher than or equal to 2 MHz.

The electronic control system and the imaging ultrasonic transducer may also be configured to monitor recanalization of a treated blood vessel by Doppler imaging.

BRIEF DESCRIPTION OF THE DRAWINGS

Other features, details and advantages of the invention will become clearer on reading the description, which is given with reference to the appended drawings, which are given by way of example and show, respectively.

DETAILED DESCRIPTION

Figure 1:
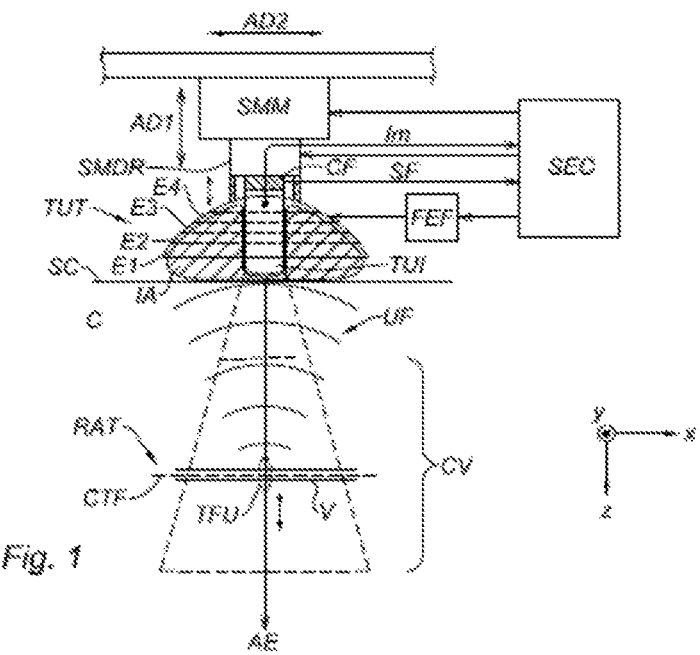
FIG. 1, a schematic of an apparatus according to one embodiment of the invention.

In the device of FIG. 1, the therapeutic ultrasonic transducer TUT is a multi-element annular transducer, i.e. it consists of a set of annular ultrasonic transducers, or elements (referenced E1, E2, E3, E4), of decreasing radii that are arranged concentrically so as to form a spherical, or more generally concave (for example paraboloid-shaped) cap. Such a transducer is for example described in document U.S. Pat. No. 5,520,188.

Of course, the number of transducers is not necessarily equal to 4; preferably, this number will be comprised between 4 and 20 to avoid an excessive complexity.

The annular elements are preferably circular; more precisely, they may have a frustoconical shape of circular base, but other shapes are envisionable. They may be continuous or be formed of discrete segments.

The ultrasonic waves UF generated by the elements E1-E4 of the therapeutic transducer TUT are focused into a focal spot TFU having a generally ellipsoidal shape. The main emission axis of the ultrasound is designated by "z". For the sake of simplicity, although this is not essential, this axis will be considered to be perpendicular to the surface SC (i.e. the skin) of the human or animal body C to be treated. The ultrasound is coupled to the body by an acoustic interface IA, for example formed by a pocket made of flexible plastic filled with gel or degassed water. This pocket has a convex face that makes contact with the elements of the transducer and a substantially planar face intended to make contact with the surface SC. In use, this planar face may in turn be coated with an acoustic coupling gel.

The concave shape of the transducer ensures the ultrasound UF is focused at a "natural" or "geometric" focal length along the axis z. Electronic focusing, obtained by introducing phase-shifts between the drive signals of the elements, allows this focal length to be finely modified. In the embodiment of FIG. 1, these drive signals are generated by an electronic control system SEC and the shifts are introduced by a beam-forming circuit FEF, which is driven by the system SEC.

Advantageously, the therapeutic transducer is configured to operate at a frequency higher than or equal to 2 MHz, equal to 2.25 MHz for example, whereas in the aforementioned prior art the frequency of the therapeutic ultrasonic waves was rather about 1 MHz. Specifically, for a given geometry of the transducer and a given focal length, the width (perpendicular to the direction of propagation) and the length (parallel to this length) of the focal spot are inversely proportional to frequency. This theoretical result has been confirmed by numerical simulations. Thus, by operating at 2 MHz rather than at 1 MHz, it is possible to divide the volume of the focal spot by a factor of 8. This allows the clot to be broken up to be better targeted and the risk of damage to the walls of the blood vessel to be minimized.

In vitro trials have confirmed the effectiveness of ultrasound at 2.25 MHz in a thrombotripsy treatment. During these trials, human blood was placed in tubes made of silicone of 6 mm inside diameter, modelling human femoral veins, and which were held in vertical position. The coagulation of the blood was induced by adding 20 nM of calcium chloride, leading to the formation of clots of 2.5 cm length. Next, the tubes were placed in horizontal position and loaded with saline solution (0.9% NaCl) at a pressure of 30 cm $H_2O$. Only tubes containing an obstructive clot were retained and subjected to a thrombotripsy treatment. This treatment was applied by means of two ultrasonic transducers operating at 2.25 MHz, having a focal length of 38 mm and a diameter also of 38 mm. The tubes, the thrombotripsy transducers and an imaging transducer were placed in a bath of degassed water. Three therapy protocols were tested: 3 passes at a speed of 1 mm/s, 2 mm/s and 3 mm/s. In every case, the two transducers were driven with pulses of 8 cycles at 2.5 kW, engendering a peak negative pressure of −15 MPa. The first protocol proved to be the optimal one, leading to an effective recanalization (80±7% of the maximum flow rate) after 3 passes, for a treatment time of 90 seconds. A very small number of debris particles of size larger than 100 μm (1.6±1.7 per thrombus) was detected, but none of size larger than 200 μm: this may be considered to represent zero danger of embolism.

An ultrasonic imaging transducer TUI, for example a two- or three-dimensional sonographic probe, is arranged at the center of the therapeutic transducer, inside the element E4 of smallest radius. This transducer has a field of view CV that mainly extends along the axis z and includes the region in which the focal spot TFU is normally found. In the embodiment of FIG. 1, more precisely, the imaging ultrasonic transducer TUI is of two-dimensional type and the field of view is located in a plane xz. The imaging control system SEC drives the imaging transducer, receives the signals Im acquired by the latter and processes them to reconstruct images of a region RAT to be treated of the body C.

Advantageously, the imaging transducer extends axially (i.e. in the direction z) beyond the outside edge of the therapeutic transducer. For example, it may extend therebeyond by 10-50 mm and preferably by 10-25 mm. The acoustic interface IA may have an aperture allowing it to be passed through by the imaging transducer or, as in the case of FIG. 1, a recess commensurate to the latter. This allows an active face of the imaging transducer to make "direct" contact (in fact, contact by way of a thin layer of acoustic coupling gel) or "indirect" contact (via a double thickness of the pocket of the acoustic interface IA, and likewise of the thin layer of gel) with the surface SC of the body C, whereas the edge of the therapeutic transducer may be spaced apart from this surface.

In the embodiment of FIG. 1, the therapeutic transducer TUT and the imaging transducer TUI are joined by way of a mechanical system SMDR allowing a relative movement thereof translationally in the direction z. For example, the imaging transducer may be fastened to a base of this mechanical system, and the therapeutic transducer joined to this base by way of three actuating cylinders (only two of which are shown in the figure) that are oriented along the axis z. Synchronously driving the three actuating cylinders with the electronic control system SEC allows the therapeutic transducer and therefore the focal spot TFU of the focused ultrasound—to be moved in the direction z, without it being necessary to move at the same time the imaging transducer. The mechanical system SMDR for achieving a relative movement may also take other forms: it may for example be based on a rack and pinion system.

The presence of the mechanical system SMDR is not essential: specifically, the multi-element structure of the therapeutic transducer and the beam-forming circuit FEF also allow the focal spot TFU of the focused ultrasound to be moved in the direction z relative to the imaging transducer. Reciprocally, the mechanical system SMDR may suffice, in which case it is not necessary to provide a multi-element transducer and an electronic focusing system. In any case, in an apparatus according to the invention it is possible to position the focal spot TFU in the axial direction without having to move the imaging transducer. In contrast, this is not possible in the apparatuses described in international patent application WO 2009/094554 and in the aforementioned articles by Xi Zhang et al., in which it is only possible to position the focal spot by moving the therapeutic transducer and the imaging transducer together.

In the embodiment of FIG. 1, the imaging transducer TUI is joined to the base of the mechanical system SMDR—or more generally to a holding part—by way of a force sensor CF, which is for example piezoelectric, allowing a force exerted on the transducer in the direction z to be measured. The force-measurement signal SF acquired by the sensor is transmitted to the electronic control system SEC. This has a dual function: on the one hand, the detection of a non-zero force makes it possible to ensure that the imaging transducer is indeed making—direct or indirect—contact with the surface SC of the body C; on the other hand, the quantitative measurement of this force makes it possible to prevent the imaging transducer from being pressed too hard against the surface SC, and squashing the tissues of the body C.

The presence of the force sensor CF is not essential. Specifically, it is also possible to use techniques for analyzing images reconstructed by the electronic control system to detect a surface SC and to determine the position thereof with respect to the transducer TUI.

The assembly comprising the therapeutic transducer TUT, the imaging transducer TUI and, where appropriate, the mechanical system SMDR for achieving a relative movement and/or the force sensor CF, is fastened to a motorized mechanical system SMM which is driven by the electronic control system SEC, allowing movement thereof with respect to a mount (and therefore with respect to the body C) with at least two degrees of freedom:

a translation along a first axis AD1, parallel to the axis z; and a translation or a rotation along or about a second axis AD2, that is not parallel—and typically perpendicular—to the first.

In the embodiment of FIG. 1, the second degree of freedom is a translation along a second axis AD2 parallel to the direction x. More precisely, in this embodiment, the motorized mechanical system SMM comprises a carriage that slides along a rail oriented along the axis AD2 ($x$) and that bears an actuating cylinder that ensures the translation along the axis AD1 ($z$). In more sophisticated embodiments provision may be made for a plurality of degrees of freedom—for example three translations and three rotations, and more particularly three translations along the orthogonal axes x, y and z and three rotations about the same axes. This may be obtained, inter alia, by means of a robotic arm.

As was described above, the electronic control system SEC performs a plurality of functions: driving the mechanical system SMDR for achieving a relative movement and the motorized mechanical system SMM, driving the therapeutic and imaging transducers, acquiring imaging signals, reconstructing and analyzing images, acquiring force-measurement signals, etc. This system may comprise one or more computers and/or dedicated digital electronic boards. These elements need not necessarily be located together, but may in particular be connected by way of a bus, a local network or even the Internet.

Figure 2:
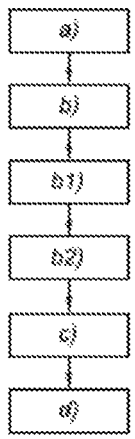
FIG. 2, a flowchart of a treatment method using such an apparatus.

An apparatus according to the invention may be used to implement a method for treating a thrombosis according to FIG. 2.

Firstly—step a)—the motorized mechanical system SMM is driven by the electronic control system SEC in order to perform a first scan of the surface SC of the body C in accordance with the region RAT to be treated. Simultaneously—step b)—the imaging ultrasonic transducer TUI is used to acquire a plurality of images of the region RAT, preferably allowing a three-dimensional reconstruction of the latter. The motorized mechanical system SMM is driven in such a way that the imaging transducer is kept at a constant distance from the surface SC, with a predefined tolerance that is generally lower than or equal to 10% and preferably than 1%. This distance is typically comprised between 0 (direct or indirect contact, this being the preferred embodiment) and 40 mm, so as to ensure a satisfactory and constant image quality during the scan. As mentioned above, furthermore, when the imaging transducer is kept in contact with the surface SC, a force-measurement signal SF may be used to keep constant (also with a tolerance generally lower than or equal to 10% and preferably than 1%) the pressure exerted by the transducer on said surface.

During this first scan, the therapeutic transducer is kept inactive.

Next—step b1) the images acquired during the first scan are analyzed by the electronic control system SEC in order to automatically identify a blood vessel to be treated (reference V in FIG. 1) in the region RAT. This step may be carried out by choosing or reconstructing a cross-sectional view of a plane (plane yz in the case of FIG. 1) approximately perpendicular to the axis of the vessel to be detected, in such a way that the vessel appears as a circle or an ellipse, and by applying a circle detection algorithm, which for example may be based on a Hough transform or a Canny-Dériche edge detector associated with an accumulator that determines the position of the center of the circle using a voting mechanism. Other known algorithms may also be used. As a variant, the blood vessel may be detected by an operator, where appropriate using thresholding of the acquired images and/or edge detection. Next—step b2)—a path or trajectory inside the body C and along the identified blood vessel V is determined. This operation may be carried out automatically by the electronic control system SEC, or manually by an operator.

Once these preparatory operations have ended, the actual therapeutic treatment may start.

The motorized mechanical system SMM is again driven by the electronic control system SEC in order to perform a second scan of the surface SC of the body C—step c). As in the first scan, the driving is such that the imaging transducer is kept at a constant distance from the surface SC (which distance is preferably comprised between 0-preferred case—and 40 mm, with a tolerance no higher than 10% or even than 1%). Also as in the first scan, when the imaging transducer is kept in contact with the surface SC, a force-measurement signal SF may be used to keep constant (also with a tolerance generally lower than or equal to 10% and preferably than 1%) the pressure exerted by the transducer on said surface.

The second scan is generally not identical to the first. Specifically, while the first scan aims to enable an exhaustive exploration of the region to be treated containing the vessel V to be treated, during the second scan the motorized mechanical system SMM is driven in such a way that the blood vessel V is located in the central region (for example, in the central third along the axis z and along an axis perpendicular to z) of the field of view CV of the imaging transducer. Advantageously, images acquired during the second scan are used to drive the motorized mechanical system in a closed-loop.

During the second scan, the therapeutic ultrasonic transducer TUT is activated and the mechanical system SMDR for achieving a relative movement and/or the beam-generating circuit FEF are/is driven in such a way that the focal spot TFU of the focused ultrasonic waves emitted by the transducer TUT follow the path defined in step b2). This is the last step—d)—of the method of FIG. 2.

Moreover, during or after the second scan, the imaging ultrasonic transducer may be used, under the control of the electronic system SEC, to acquire Doppler echography images in order to monitor the recanalization of a treated blood vessel by Doppler imaging.

The invention claimed is:

1. An apparatus for treating vascular thrombosis with ultrasound, comprising:
   a therapeutic ultrasonic transducer (TUT), suitable for generating focused ultrasonic waves (OUF) that propagate along an emission axis (AE);
   an imaging ultrasonic transducer (TUJ) associated with the therapeutic ultrasonic transducer, configured to acquire two- or three-dimensional images (Im) of a region (RAT) to be treated of a human or animal body (C), the region to be treated including a focal spot (TFU) of the therapeutic ultrasonic transducer;
   a means (SMDR, FEF) for moving the focal spot of the therapeutic ultrasonic transducer along the emission axis with respect to the imaging ultrasonic transducer;
   further comprising:
   a motorized mechanical system (SMM) configured to move the therapeutic ultrasonic transducer and the imaging ultrasonic transducer translationally along at least a first axis of movement (AD1) parallel to said emission axis, and translationally or rotationally along or about a second axis of movement (AD2) not parallel to the first; and
   an electronic control system (SEC) configured to:
   drive the motorized mechanical system so as to perform a scan of the region to be treated; and
   drive the means (SMDR, FEF) for moving the focal spot of the therapeutic ultrasonic transducer so as to control a position of the focal spot along the emission axis during said scan while keeping constant, with a predefined tolerance, a distance between the imaging ultrasonic transducer and a surface (SC) of the human or animal body; and
   wherein the electronic control system is also configured to:
   a) drive the motorized mechanical system so as to perform a first scan of the region to be treated;
   b) during this first scan, acquire a plurality of images of said region while keeping the therapeutic ultrasonic transducer inactive;
   b1) analyze the plurality of images acquired during the first scan in order to identify a blood vessel (V) in the region to be treated of said human or animal body;
   b2) determine said predefined path inside said human body in such a way that it corresponds to said blood vessel;
   c) drive the motorized mechanical system so as to perform a second scan of the region to be treated; and
   d) during this second scan, activate the therapeutic ultrasonic transducer and drive the means (SMDR, FEF) for moving its focal spot in such a way that said focal spot follows a predefined path inside said human body, which is identified from the plurality of images acquired during the first scan.

2. The apparatus as claimed in claim 1, also comprising a force sensor (CF) suitable for generating a signal (Sf) indicative of a force exerted on the imaging ultrasonic transducer in a direction parallel to said emission axis, the electronic control system being configured to acquire this signal and to use it to drive the motorized mechanical system so as to keep said imaging ultrasonic transducer in contact with said surface of the human or animal body during the scan.

3. The apparatus as claimed in claim 2, wherein the electronic control system is also configured to apply said imaging ultrasonic transducer against said surface of the human or animal body during the scan with a constant force.

4. The apparatus as claimed in claim 1, wherein the electronic control system is also configured to analyze images acquired by the imaging ultrasonic transducer so as to detect the surface of said human or animal body in order to drive the motorized mechanical system during said scan.

5. The apparatus as claimed in claim 1, wherein the electronic control system is also configured to drive the motorized mechanical system in such a way that, during the second scan, said blood vessel is located in a central portion of a field of view (CV) of the imaging ultrasonic transducer.

6. The apparatus as claimed in claim 5, wherein the electronic control system is also configured to acquire a plurality of images of the region to be treated during the second scan and to use these images to drive the motorized mechanical system.

7. The apparatus as claimed in claim 1, wherein the therapeutic ultrasonic transducer is a multi-element transducer and the means (SMDR, FEF) for moving its focal spot comprises an electronic beam former (FEF) configured to drive the elements (E1, E2, E3, E4) of said transducer with variable delays in order to emit the focused ultrasonic waves with an adjustable focal length.

8. The apparatus as claimed in claim 7, wherein the therapeutic ultrasonic transducer is a concentric multi-ring transducer.

9. The apparatus as claimed in claim 1, wherein the means (SMDR, FEF) for moving the focal spot of the therapeutic ultrasonic transducer comprises a mechanical system (SMDR) allowing a relative movement, along said emission axis, of the therapeutic ultrasonic transducer and of the imaging ultrasonic transducer.

10. The apparatus as claimed in claim 1, wherein the imaging ultrasonic transducer extends beyond, in a direction parallel to said emission axis, the therapeutic ultrasonic transducer.

11. The apparatus as claimed in claim 1, wherein the imaging ultrasonic transducer is arranged at the center of the therapeutic ultrasonic transducer.

12. The apparatus as claimed in claim 1, also comprising an acoustic interface device (IA) configured to couple the focused ultrasonic waves generated by the therapeutic ultrasonic transducer to said surface of the human or animal body.

13. The apparatus as claimed in claim 1, wherein said motorized mechanical system has three degrees of freedom translationally and three degrees of freedom rotationally.

14. The apparatus as claimed in claim 1, wherein said therapeutic ultrasonic transducer is suitable for generating focused ultrasonic waves at a frequency higher than or equal to 2 MHz.

15. The apparatus as claimed in claim 1, wherein the electronic control system and the imaging ultrasonic transducer are also configured to monitor recanalization of a treated blood vessel by Doppler imaging.

* * * * *